(12) United States Patent
Böhm et al.

(10) Patent No.: US 11,004,184 B2
(45) Date of Patent: May 11, 2021

(54) METHOD AND IMAGING DEVICE FOR GENERATING A ROADMAP IMAGE

(71) Applicant: Siemens Healthcare GmbH, Erlangen (DE)

(72) Inventors: Stefan Böhm, Oberasbach (DE); Philipp Bernhardt, Forchheim (DE); Andreas Berting, Schlüchtern (DE)

(73) Assignee: Siemens Healthcare GmbH, Erlangen (DE)

( * ) Notice: Subject to any disclaimer, the term of this patent is extended or adjusted under 35 U.S.C. 154(b) by 30 days.

(21) Appl. No.: 16/458,322

(22) Filed: Jul. 1, 2019

(65) Prior Publication Data
US 2020/0013152 A1 Jan. 9, 2020

(30) Foreign Application Priority Data

Jul. 6, 2018 (EP) .................................. 18182181

(51) Int. Cl.
*G06T 5/50* (2006.01)
*G06T 5/00* (2006.01)
*G06T 7/00* (2017.01)

(52) U.S. Cl.
CPC ............... *G06T 5/50* (2013.01); *G06T 5/002* (2013.01); *G06T 7/0012* (2013.01); *G06T 2207/10121* (2013.01)

(58) Field of Classification Search
CPC ......... G06T 5/50; G06T 5/002; G06T 7/0012; G06T 2207/10121; A61B 6/5258; A61B 6/54; A61B 6/5235; A61B 6/481; A61B 6/487; A61B 6/504; A61B 6/4441; A61B 6/463; A61B 6/5211
See application file for complete search history.

(56) References Cited

U.S. PATENT DOCUMENTS 8,891,843 B2 * 11/2014 Ohishi .................. A61B 6/481
382/128
10,147,171 B2 * 12/2018 Brown .................. A61B 6/487
(Continued)

FOREIGN PATENT DOCUMENTS

EP        3320843 A1    5/2018
JP    2010183388 A *   8/2010

OTHER PUBLICATIONS

European Search Report for European Patent Application No. 18182181.0 dated Feb. 11, 2019.

*Primary Examiner* — Nancy Bitar
*Assistant Examiner* — Nicholas P Kellogg
(74) *Attorney, Agent, or Firm* — Lempia Summerfield Katz LLC

(57) ABSTRACT

The disclosure relates to a method and an imaging device for generating a new roadmap image of a target object. For the method, a first subtraction image is generated from a first mask image and a contrast agent image of the target object. A parameter value of a parameter of the imaging device that affects the acquisition of images by the device is then changed. A third mask image of the target object is acquired automatically by the imaging device using the changed parameter value. From a second examination image subsequently acquired using the changed parameter value, a third subtraction image is generated by subtraction of the third mask image. The new roadmap image is generated using the first subtraction image and the third subtraction image.

19 Claims, 3 Drawing Sheets

(56) References Cited

U.S. PATENT DOCUMENTS

| | | | |
|---|---|---|---|
| 2003/0039331 A1* | 2/2003 | Rick | G06T 5/50 378/50 |
| 2008/0296507 A1* | 12/2008 | Petrick | G01T 7/005 250/370.09 |
| 2009/0180591 A1* | 7/2009 | Baumgart | A61B 6/504 378/98.12 |
| 2009/0180676 A1* | 7/2009 | Pfister | A61B 6/504 382/130 |
| 2013/0034283 A1* | 2/2013 | Ohishi | A61B 6/12 382/128 |
| 2015/0310597 A1* | 10/2015 | Ohguri | H04N 5/2254 382/275 |
| 2017/0228863 A1* | 8/2017 | Bernhardt | A61B 6/5235 |
| 2018/0082420 A1* | 3/2018 | Brown | A61B 6/5205 |
| 2018/0374204 A1 | 12/2018 | Manhart | |
| 2020/0179045 A1* | 6/2020 | Levin | A61B 18/1492 |

* cited by examiner

METHOD AND IMAGING DEVICE FOR GENERATING A ROADMAP IMAGE The present patent document claims the benefit of European Patent Application No. EP 18182181.0, filed Jul. 6, 2018, which is also hereby incorporated by reference.

TECHNICAL FIELD

The disclosure relates to a method for generating a roadmap image of a target object by an imaging device and to an appropriately configured imaging device. The imaging device may be a medical imaging device such as an X-ray unit. A roadmap image is an image generated according to the roadmap method well-known per se, particularly in the technical field of medical imaging.

BACKGROUND

In the roadmap method, two images may be superimposed on one another in order to facilitate orientation or navigation. These two images are, for example, a live X-ray or fluoroscopic image which shows a current situation or a current state of the target object, and an orientation image. The roadmap method is also a double subtraction method. This means that the two images superimposed on one another to generate the roadmap image are themselves subtraction images or subtracted images. In particular, two-dimensional (2D) images are used here.

In general, the problem with using the roadmap method is that when, for example, a zoom function is applied, respective physical image acquisition conditions change, so that the subtraction images may not be generated or superimposed in an artifact-free manner. This means that such imaging device functions have hitherto been virtually unusable during the roadmap procedure, or at least not with any information gain. Nowadays, for example, only a digital zoom is therefore used whereby, although no image acquisition conditions are changed and no subtraction or superimposition artifacts are therefore produced, on the other hand there is no objective information gain either, e.g. no enhanced detail resolution or the like.

SUMMARY AND DESCRIPTION

The object of the present disclosure is to enable the roadmap method to be used more flexibly and with improved image quality.

The scope of the present disclosure is defined solely by the appended claims and is not affected to any degree by the statements within this summary. The present embodiments may obviate one or more of the drawbacks or limitations in the related art.

A method is used to generate at least one new roadmap image of a target object obtained by an imaging device, (e.g., by a medical imaging device). The imaging device may be an X-ray unit, (e.g., a fluoroscopy unit). The target object may be any object suitable for mapping or representation by the imaging device. The method may be used, for example, in a medical environment for imaging a patient or biological tissue, or in an industrial context.

For example, like any surgical intervention that may be carried out simultaneously with the method, the injection or introduction of a contrast agent or similar is explicitly not part of the method. The method is therefore explicitly not a surgical procedure. The method may rather be regarded as a method for operating an imaging device. Likewise, the method may be used, for example, to process already acquired and provided images or image data and is therefore independent of any direct medical or surgical procedure.

In the method, initially a first roadmap image is generated by superimposition of a first and a second subtraction image, wherein the first subtraction image is generated from a first mask image of the target object acquired by the imaging device and a contrast agent image of the target object likewise acquired by the imaging device. For this purpose, the first mask image may be acquired prior to flooding of the target object with an X-ray contrast agent, and the contrast agent image thereafter. The second subtraction image is generated from a second mask image acquired by the imaging device and a first examination image of the target object likewise acquired by the imaging device. Here, the first mask image may be used as the second mask image or it may be acquired separately. The examination image is an image of the target object acquired after the contrast agent image and after the second mask image.

In particular, the four images used to generate the first and second subtraction image are acquired in the sequence as stated here. In other words, the first mask image is therefore acquired at a first point in time, the contrast agent image at a later second point in time, the second mask image at an even later third point in time, and the first examination image, later again, at a fourth point in time. This applies insofar as the first mask image is not used as the second mask image. To generate the subtraction images, the respective mask image is subtracted from the respective other image involved. This means that corresponding pixel or intensity values of the respective images are subtracted from one another, so that the resulting subtraction images show or represent a difference between the respective images.

The fact that the two subtraction images for generating the first roadmap image are superimposed on one another may, but need not necessarily, mean that the subtraction images or their pixel or intensity values of their mutually corresponding pixels are added in respect of their position, e.g., in respect of a sub-region of the target object represented by them. The superimposition or superimposing may also mean applying a more complex combination function by which one or both of the superimposed, (e.g., combined), subtraction images for generating the roadmap image are modified.

After the first roadmap image has been generated, or after acquisition of the at least four images used for generating the first and second subtraction image, a parameter value of a physical parameter of the imaging device is changed, the parameter affecting the acquisition of images of the target object by the imaging device. The parameter whose value is changed here is therefore an imaging or image acquisition parameter of the imaging device. Here, such a parameter or parameter value that is changed may be, for example, a zoom level used for image acquisition, an aperture or aperture size or aperture shape used, a collimator setting, a voltage of an X-ray tube of the imaging device, a radiation output or radiation dose per image, and/or similar. In other words, the parameter value change envisioned here means that image artifacts may be produced when a subtraction image is generated from an image acquired before and after the changing of the parameter value. In particular, it is therefore provided that at least the first mask image and the contrast agent image on the one hand and the second mask image and the first examination image on the other are acquired with the same setting of the corresponding parameter, that is to say with identical parameter values, e.g., under identical physical conditions in respect of the imaging or image acquisition. In comparison, target object images acquired after changing of the parameter value are acquired using the new, e.g., changed parameter value and, accordingly, under changed physical acquisition conditions.

The parameter value may be changed e.g. manually by a user or operating personnel. However, the parameter value may also be changed, e.g., automatically by the imaging device itself according to a predefined program. The changing of the parameter value may be carried out at least semi-automatically by the imaging device on receiving an appropriate control or data signal. The changing of the parameter value is to be understood as being by way of example here, as a plurality of corresponding parameter values of the one or more parameters may be changed.

Immediately after changing of the parameter value, a third mask image of the target object is acquired automatically by the imaging device using the changed parameter value. The third mask image therefore represents the state of the target object after changing of the parameter value. As the third mask image has been acquired using the changed parameter value, it may advantageously be used as a mask image for generating further subtraction images from further images of the target object subsequently acquired likewise using the changed parameter value without artifacts, aliasing errors or the like being produced. This automatic acquisition of the third mask image is particularly advantageous, as it enables a user to concentrate fully on examining the target object, without having to worry about the changing of the parameter value possibly causing image artifacts. Acquiring the third mask image immediately after the changing of the parameter value means that the third mask image is acquired in a predefined period after changing of the parameter value, e.g., as the first image of the target object after the parameter value has been changed. In particular, the third mask image is acquired, for example, before further contrast agent, an auxiliary or foreign object, a medical device, or similar is introduced into the field of view of the imaging device or into the target object itself.

It may be provided that a control stop is automatically set for the imaging device each time a mask image has been acquired. The control stop may be set, e.g., maintained such as for a predefined period of time, and/or until such time as at least one further image, e.g., a respective examination image, has been acquired. The control stop prevents changes from being made to the imaging or image acquisition, e.g., the parameters or parameter values of the imaging device which affect the acquisition conditions. This provides that respective images may be superimposed or combined in as artifact-free a manner as possible and, for example, that, for a particular parameter setting, not just a single image for which then, for example, no mask image acquired using the same parameter setting otherwise exists is acquired.

In addition, at least one third subtraction image of the target object is generated from at least one second examination image of the target object acquired after the third mask image using the changed parameter value by subtraction of the third mask image from the second examination image. This third subtraction image is therefore generated analogously to the generation of the second subtraction image, except that the changed parameter value as compared to the first and second mask image is used for both the second examination image and the third mask image. The fact that at least one second examination image is acquired and at least one third subtraction image is generated accordingly means that, for example, the third mask image for generating a corresponding respective third subtraction image may be subtracted from each examination image acquired after the third mask image in each case.

After the third mask image, a plurality of examination images may therefore be acquired which may be designated as second examination images or consecutively numbered accordingly, e.g., as second examination image, third examination image, fourth examination image, etc. Accordingly, a designation of subtraction images generated from these examination images may be in line with the numbering or nomenclature used for the examination images, so that a plurality of third subtraction images may therefore be generated for different examination images, wherein the plurality of third subtraction images may then likewise be designated as, for example, a third subtraction image, a fourth subtraction image, a fifth subtraction image, etc.

The method is applied, in particular, until such time as the third mask image is acquired, e.g., for examination images for whose acquisition the same parameter value of the previously changed parameter is used. This provides that the at least one third subtraction image or the plurality of third subtraction images contain no image artifacts resulting from a further change of parameter value, e.g., of the physical acquisition conditions.

The at least one new roadmap image of the target object after changing of the parameter value is generated using the first subtraction image and the at least one third subtraction image. If a plurality of third subtraction images have therefore been previously generated, a respective new roadmap image may thus be generated from each of these third subtraction images using the first subtraction image in each case.

If, after acquisition of the second examination image or after generation of the third subtraction image or of the new roadmap image the parameter value is reset to its original or previous value, respective subtraction images may be generated from further subsequently acquired examination images by subtraction of the second mask image or of the first mask image and used for further new roadmap images.

The method may also be continued iteratively according to the scheme described. This means that after the described changing of the parameter value and acquiring of the second examination image, the parameter value may be changed again to a previously unused value. In such a case, images acquired between the first and the second change of parameter value may assume the corresponding roles of the images acquired in the previous iteration act prior to the first change of the parameter value. For example, at least the third subtraction image may then be used as the second subtraction image according to the above described method. However, the original first subtraction image may possibly also be re-used as such after the further or second change of the parameter value.

Although not explicitly described in detail here, the respective images, (e.g., the mask images, the contrast agent image, the examination images, the subtraction images and/or the roadmap images), may be pre- and/or post-processed by an image processing method. This enables, for example, the image quality or recognizability of individual details to be improved, noise to be suppressed, and/or further processing to be facilitated. For example, prior to the respective generation of the subtraction images, a logarithmic filter may be applied to the images used for that purpose, e.g., the images may be logarithmized.

The method for generating a new roadmap image is a method or may be regarded or used as a method for automatically or semi-automatically operating or controlling the imaging device, wherein the imaging device includes a corresponding image generating or data processing device for processing and generating the different target object images described. The method described herein is therefore explicitly not a surgical procedure, nor does the method include any surgical method act, although the method may be used in a medical field of application.

The method advantageously provides that two images that have been acquired with the same parameter value, e.g., using the same parameter value or the same parameter values, are used for the subtraction images in each case. This therefore provides that no corresponding image defects or artifacts occur in the subtraction images described and therefore the roadmap images also exhibit a correspondingly good or full image quality. The method therefore enables changed acquisition conditions or corresponding functions which require changing of the parameter value to be used even during, e.g., when using, the roadmap method. As described, a plurality of parameter values of the physical parameter or of a plurality of physical parameters of the imaging device may self-evidently also be changed in a similar manner. The method may therefore advantageously provide an information gain in a region of the target object or for that imaged after changing of the parameter value, e.g., in the form of a higher resolution of a sub-region of the target object and/or in the form of a higher signal-to-noise ratio or the like. In particular, this is not at the expense of poorer image quality. As opposed to a conventionally used digital zoom, a genuine or optical zoom may therefore be used, for example, which is able to provide this information gain. Lastly, the method therefore allows more accurate, more detailed, more reliable and/or safer imaging, examination or assessment of the target object when using the roadmap method.

In an advantageous embodiment, an auxiliary subtraction image is automatically generated by subtracting the second mask image or the first mask image from an examination image of the target object acquired in particular most recently or immediately prior to the changing of the parameter value. A combined subtraction image is then generated automatically by combining the auxiliary subtraction image with the third subtraction image. The combined subtraction image is used together with the first subtraction image to produce the new roadmap image. If the parameter value is changed immediately after acquisition of the first examination image, the auxiliary subtraction image may correspond to the second subtraction image. However, after acquisition of the first examination image and prior to changing of the parameter value, at least one further examination image of the target object, (e.g., a plurality of further examination images), may be acquired.

Due to the fact that the auxiliary subtraction image is generated from the most recently acquired of these further examination images, the auxiliary subtraction image therefore contains, in particular, a total image content built up until the changing of the parameter value, e.g., in respect of a spread or distribution of a contrast agent and/or of a spread or positioning of some other material such as, for example, an at least partially X-ray opaque glue or the like. As a result of the auxiliary subtraction image being used for generating the new roadmap image, it may therefore be advantageously provided that the image content built up until the changing of the parameter value is contained, (e.g., is visible), in the new roadmap image. Without the use or inclusion of the auxiliary subtraction image in the new roadmap image, this image content built up until the changing of the parameter value would be at least partially lost, as it is subtracted as part of the third mask image.

This embodiment provides a particularly advantageous method of changing the parameter value, e.g., of using corresponding functions of the imaging device, during the roadmap method with corresponding information gain, but while at least retaining the entire image content that has been built up or acquired. A chronological development of the target object or in the target object is therefore consistently comprehensible and trackable for the respective user or observer continuously from a point in time prior to the changing of the parameter value to a point in time after the changing of the parameter value, e.g., spanning the changing of the parameter value, by the most recently generated new roadmap image.

This constitutes a considerable improvement over the existing prior art. The present disclosure may achieve a significant expansion and increased quality of the currently available functionality of corresponding imaging methods, devices, or systems using the roadmap method. This is particularly the case when applying or using corresponding functions which accompany the changing of the or a corresponding parameter value. Effectively, therefore, the present disclosure for the first time makes it meaningful to use these functions or functionalities in conjunction with, (e.g., during), the roadmap method, e.g., with sufficient image quality for practical applications. Finally, examinations of the target object may therefore be carried out faster and with less load placed on the target object.

In an advantageous development, in response to a corresponding control command to change the parameter value, prior to the execution thereof, (e.g., before the parameter value is actually changed), an auxiliary examination image of the target object is automatically acquired by the imaging device. The auxiliary examination image is then used as the examination image acquired, in particular, most recently or immediately, prior to the changing of the parameter value, for generating the auxiliary subtraction image. This provides an advantageous method of automatically providing that a total image content built up until the changing of the parameter value is actually contained in the auxiliary subtraction image, as a time lag from the acquisition of the examination image used for generating the auxiliary subtraction image, (e.g., the auxiliary examination image), to the physical changing of the parameter value may be minimized. This advantageously provides a particularly reliable and accurate method of providing continuity and consistency of the image content represented or contained in the new roadmap image. Users' workload is also reduced, as they do not have to manually initiate or carry out two functions or operator control actions themselves, namely acquiring the auxiliary examination image and changing the parameter value, as closely together as possible. This may ultimately help to achieve an improved or more reliable result of an examination or assessment of the target object and reduce the error rate in operating the imaging device.

In an advantageous development of the method, the auxiliary subtraction image and the combined subtraction image are generated as zero-mean images in each case, so that a respective average of their pixels or intensity values is zero or at least virtually zero. In other words, the auxiliary subtraction image and the combined subtraction image are therefore generated such that their pixel values are distributed around zero, wherein self-evidently not all the pixel values are per see equal to zero. As a result, particularly simple further processing of these images and ultimately particularly high image quality of the new roadmap image may be advantageously achieved. The at least one third subtraction image may also be generated in a corresponding manner as a zero-mean image.

In an advantageous development, the third subtraction image is added to the auxiliary subtraction image to generate the combined subtraction image. This means that the pixel or intensity values of the third subtraction image and of the auxiliary subtraction image are added together pixel by pixel and a corresponding sum is used as the pixel or intensity value for a respective corresponding pixel of the combined subtraction image. Combining of the auxiliary subtraction image with the third subtraction image here therefore means the addition thereof. The combined subtraction image may thus be generated particularly quickly and simply, which facilitates real-time use of the method.

It is provided, as in the case of all superimpositions or combinations of two images within the meaning of the present disclosure, that two images superimposed on one another or combined with one another have been or are registered with one another or to one another. This means that superimposed or combined pixels of two images represent or map the same sub-region of the target object in each case. If necessary, e.g., if the imaging device and/or the target object has moved between the acquisition of the respective two superimposed or combined images, registration or re-registration may be carried out accordingly, in particular, automatically.

In an advantageous development, to generate the combined subtraction image, pixel values of the auxiliary subtraction image are automatically multiplied by a predefined factor other than 1 prior to the combining of the auxiliary subtraction image with the third subtraction image. If the predefined factor is less than 1, an image portion of the new roadmap image which represents the target object or the state thereof prior to the changing of the parameter value will appear attenuated compared to an image portion of the roadmap image which represents the target object or the state thereof after the changing of the parameter value. As a result, the effect of changing the parameter value may advantageously be made visible in a particularly simple manner. This also advantageously provides a simple method of illustrating a chronological development in the one new roadmap image. If the predefined factor is set to 0, this corresponds to complete suppression of the image content built up until the changing of the parameter value. The factor may have been or be predefined, e.g., according to the application, situation, requirement, or customer request. The factor or the value thereof may be set or predefined via a user interface of the imaging device. This advantageously enables the imaging device and the method to be used in a particularly flexible manner.

In an advantageous development, to generate the combined subtraction image, a color value or a color display of the auxiliary subtraction image and/or of the third subtraction image is automatically changed, so that a combined subtraction image portion originating from the auxiliary subtraction image has a different display color from that of a combined subtraction image portion originating from the third subtraction image. In other words, the chronological sequence or change over time and thus in particular an effect of the changing of the parameter value is therefore represented by appropriate portion-wise or region-wise color coding. This allows particularly simple and clearly understandable recognizability or distinguishability of image contents representing the different points in time or states or acquisition conditions.

In an advantageous development, to generate the combined subtraction image, prior to the combining of the auxiliary subtraction image with third subtraction image, an image region in which the third subtraction image has an image content not present in the auxiliary subtraction image or an image content changed with respect thereto is automatically determined by comparison of the auxiliary subtraction image with the third subtraction image. In the image region thus determined, the third subtraction image therefore contributes additional or new image information, namely the corresponding image content, to the combined auxiliary subtraction image. The image region determined may therefore be a sub-region of the third subtraction image. However, as the images may have been superimposed pixel by pixel anyway, this image area therefore also automatically corresponds in respect of its arrangement and size to a corresponding image region or sub-region of the auxiliary subtraction image and of the combined subtraction image.

In this embodiment, a predefined threshold value filter is then applied to a sub-region of the auxiliary subtraction image corresponding to the particular image region for noise suppression. In other words, prior to the combining of the auxiliary subtraction image with the third subtraction image, by applying thresholding, the noise is therefore automatically removed precisely in the image region or in the image or sub-regions of the auxiliary subtraction image in which the image content not present in the auxiliary subtraction image, e.g., new or additional image content contributed by the third subtraction image, is present. In this way, the new or additional image content may be selectively mapped or represented in a particularly clear and low-noise manner. At the same time, during application of the threshold value filter, no information is lost in the other or remaining image regions, as the threshold value filter is not applied there. In particular, all the pixel or intensity values of the auxiliary subtraction image may be set to 0, for example, in the particular image region by the threshold value filter. In any case, this embodiment of the method provides an optimized image quality that is situation-specific, e.g., matched to the respective individual case.

In an advantageous development, after a corresponding control command to change the parameter value has been received, a plurality of auxiliary examination images of the target object is acquired automatically by the imaging device prior to the execution thereof, e.g., prior to the actual changing of the parameter value. This plurality of auxiliary examination images is then automatically averaged in order to reduce noise in the auxiliary subtraction image. For this purpose, an averaged examination image generated by averaging the plurality of auxiliary examination images may be used as the examination image used for generating the auxiliary subtraction image. Due to the fact that the plurality of auxiliary examination images is acquired automatically and only after the control command to change the parameter value has been received, the noise in the resulting auxiliary subtraction image may thus be reduced in a simple and reliable manner without the image content already built up until this point in time being lost or laborious registration being necessary. Altogether, an improved image quality may ultimately be achieved in a particularly simple manner.

In an advantageous development, for acquiring the plurality of auxiliary examination images, an image acquisition frequency or pulse rate of the imaging device is automatically increased compared to the corresponding value used hitherto. In other words, the plurality of auxiliary examination images is therefore acquired more quickly or with a shorter time lag between them than the images acquired up to that point. This is particularly advantageous for a least two different reasons. On the one hand, it enables the plurality of auxiliary examination images to capture a maximally identical state of the target object. Whereas for the previous and subsequent acquisitions or images it may be useful to allow a predefined minimum time to elapse between two images or acquisitions in order, for example, to wait for further spreading of a contrast agent or the like, this is not necessary for the plurality of auxiliary examination images, as they are used here solely as an additional database for noise reduction. A maximized image acquisition frequency is therefore particularly advantageous for acquiring the plurality of auxiliary examination images.

On the other hand, the increased image acquisition frequency makes it possible to reduce the delay between the giving/receiving of the control command to change the parameter value and the execution or implementation thereof. If a zoom or zoom level is used as the parameter, the increased image acquisition frequency or pulse rate therefore enables the transition time to a zoomed representation to be shortened. In addition to the plurality of auxiliary examination images, the previously mentioned first examination image may also be used in a similar manner.

Particularly advantageously, it may be provided that the image acquisition frequency or pulse rate is automatically reset by the imaging device to its previous value, e.g., reduced accordingly, after acquisition of the plurality of auxiliary examination images. This avoids placing an unnecessary load on the imaging device and/or the target object.

Another aspect of the present disclosure is a data storage device or data medium containing stored program code and which encodes or represents the procedural acts of at least one embodiment of the method for generating a roadmap image. The program code is designed to be executed by a processor device to carry out the corresponding encoded method.

Another aspect of the present disclosure is an imaging device, (e.g., a medical imaging device), including a data processing device for automatically processing target object images acquired by the imaging device. The data processing device includes a data storage device and a processor device connected thereto for executing the program code stored in the data storage device. In other words, the imaging device is therefore designed to carry out or execute at least one embodiment of the method. Consequently, the imaging device may be the imaging device referred to in connection with the method. The imaging device may therefore have, accordingly, the characteristics and/or components described in connection with the method. This may relate to the user interface. The imaging device may be an X-ray unit or fluoroscopy unit.

The characteristics and developments of the method and the corresponding advantages of the method provided herein may be transferred analogously to the other aspects of the disclosure, e.g., to the data storage device and the imaging device, and/or components and devices that are used or may be used to carry out the method and vice versa. The disclosure therefore also includes such developments of the method, of the data storage device and of the imaging device which have embodiments which, to avoid unnecessary redundancy, are not explicitly described separately here in the respective combination for all the aspects of the disclosure.

BRIEF DESCRIPTION OF THE DRAWINGS

Further features, details, and advantages of the present disclosure will emerge from the following description of exemplary embodiments and with reference to the accompanying drawings in which.

DETAILED DESCRIPTION

Figure 1:
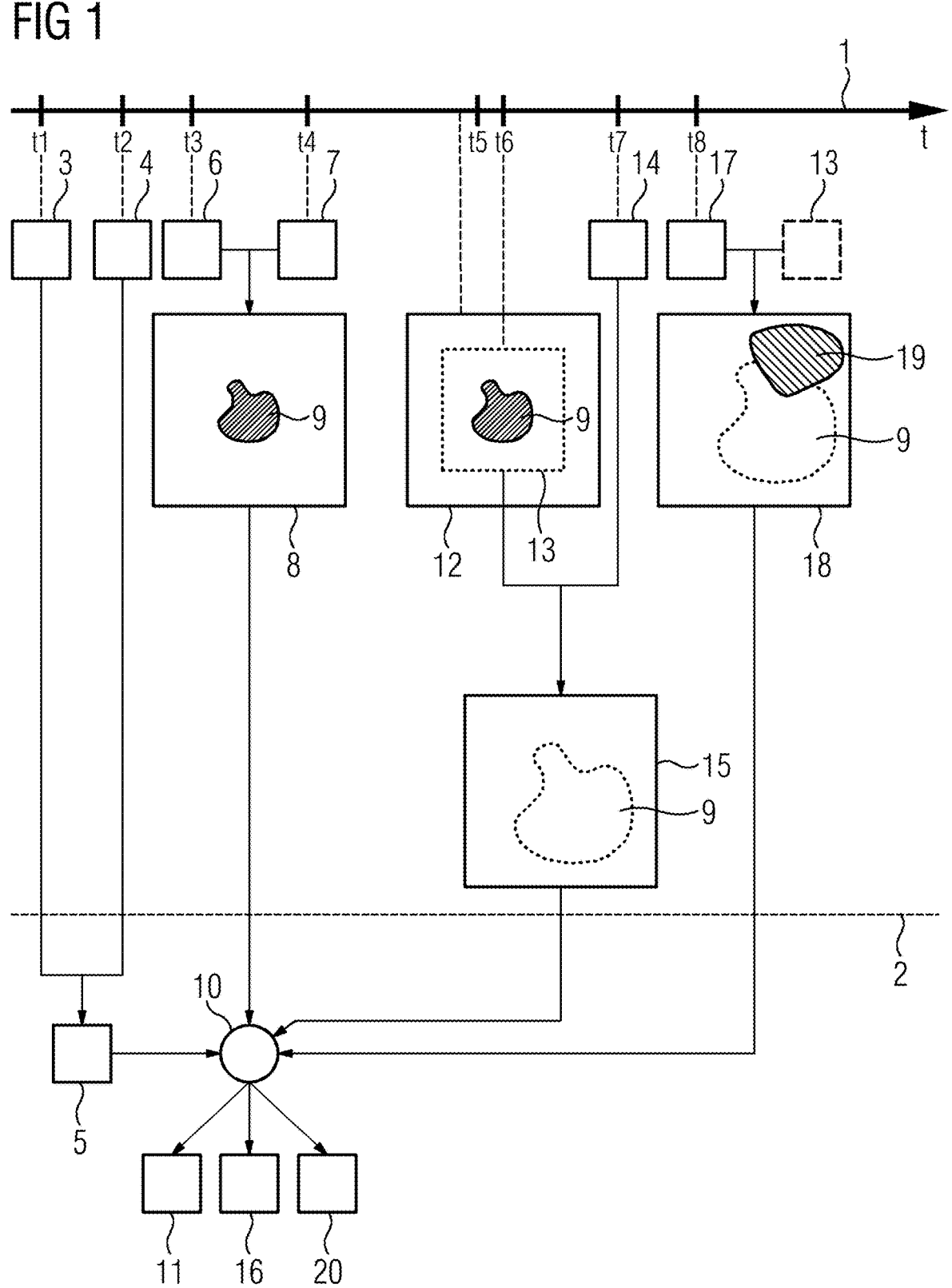
FIG. 1 depicts a schematic overview to illustrate a first variant of a method for generating an image of a target object.

The examples explained in the following are embodiments of the disclosure. In these examples, the described components of the embodiments each constitute individual features of the disclosure that are to be considered independently of one another and which in each case also develop the disclosure independently of one another and are therefore also be regarded as part of the disclosure either individually or in a combination other than that shown. In addition, the embodiments described may also be supplemented by other of the already described features of the disclosure.

In the figures, the same or corresponding elements are denoted by the same reference characters in each case.

FIG. 1 depicts a schematic overview illustrating a first variant of a method for generating an image of a target object using a roadmap method. This overview shows a time axis 1. Marked on this time axis 1 are a plurality of points in time t1 to t8 at which different procedural acts of the method are carried out. Time t1 represents the earliest point in time and time t8 the latest point in time.

A chronological coincidence or association of displayed elements with the time axis 1 applies only to elements shown between the time axis 1 and an auxiliary line 2. In particular, elements shown underneath, (on the opposite side of the auxiliary line 2 from the time axis 1), may possibly be carried out or be relevant at points in time other than their arrangement relative to the time axis 1 would suggest. This also applies in a corresponding manner to FIG. 2 explained further below.

At time t1, a first mask image 3 of the target object is first acquired by a medical imaging device, (e.g., by an X-ray unit). The target object may be a patient or a particular sub-region of the patient. The first mask image 3 is acquired, in particular, before a contrast agent or the like is introduced into the field of view of the imaging device or is injected into the target object. After acquisition of the first mask image 3, the contrast agent may be injected into the target object and spread therein. At a time t2, an injection or contrast agent image 4 of the target object is then acquired. The first mask image 3 and the contrast agent image 4 are acquired using the same X-ray-physical parameters or settings of the imaging device.

After the first mask image 3 and the contrast agent image 4 have been acquired, a first subtraction image 5 is generated therefrom by subtracting the first mask image 3 from the contrast agent image 4. In this example, the first subtraction image 5 is a vessel map, e.g., an image of a vascular tree.

At a time t3, a second mask image 6 and, at a time t4, a first examination image 7 of the target object is acquired. The second mask image 6 and the first examination image 7 are also acquired using the same X-ray-physical parameters or parameter values of the imaging device, e.g., under the same acquisition conditions. These parameter values or acquisition conditions may be the same as the parameter values or settings or acquisition conditions, used for the first mask image 3 and the contrast agent image 4. However, different parameter values or settings, e.g., acquisition conditions, may also be used for the first mask image 3 and the contrast agent image 4 on the one hand and for the second mask image 6 and the first examination image 7 on the other. This provides that a corresponding subtraction image may be generated from the two images in an artifact-free manner in each case.

A second subtraction image 8 is generated by subtraction of the second mask image 6 from the first examination image 7. The second subtraction image 8 here shows a first image content 9 which has built up between time t3 and time t4. If the method is used, for example, while an arteriovenous malformation (AVM) is being sealed off using a radio- or X-ray-opaque glue in an interventional procedure, the second subtraction image 8 or the first image content 9 may represent a distribution of the glue injected into the target object or into the field of view after time t3. The second subtraction image 8 may also be generated at a point in time later than that shown here.

The first subtraction image 5 and the second subtraction image 8 are then combined with one another, e.g., superimposed on one another, by applying a combination function 10. This produces a first roadmap image 11 which shows, as a double subtraction image, both the vascular pattern and the first image content 9, e.g., the glue and/or other miniature tools such as a stent, a catheter or similar, for example. The second subtraction image 8 may accordingly also be termed an equipment or device image. Here, it is assumed that only 2D images are processed, or combined with one another or superimposed.

The generation of the subtraction images 5, 8 may therefore be expressed as:

$$VM=P(t2)-P(t1) \text{ and } DV(t4)=P(t4)-P(t3)$$

where VM denotes the first subtraction image 5, DV(t4) the second subtraction image 8 generated from the first examination image 7 acquired at time t4, and P(tx) with x∈[1,8] the image acquired at time tx in each case. The generation of the first roadmap image 11 may accordingly be expressed as:

$$RDMP(tx)=K[VM,DV(tx)]$$

where RDMP(tx) is the roadmap image which is generated from an examination image acquired at time tx, and K[ ] the combination function with the arguments VM and DV(t). The images VM and DV(t) for generating the roadmap image RDMP(tx) are therefore combined with one another in this case by the combination function K[ ].

In this example it is provided that, at a time t5, the imaging device zoom level used to acquire the images 3, 4, 6, 7 is changed. The zoom level is an X-ray-physical parameter of the imaging device, the value of which causes the acquisition conditions to change. Images acquired after time t5 may not therefore simply be combined with images acquired prior to time t5 in order to generate a corresponding subtraction image, in particular, not without unwanted image artifacts being produced. For this reason, an auxiliary subtraction image 12 is generated immediately prior to time t5 in this case. For this purpose, the second mask image 3 is subtracted from an examination image of the target object (not shown individually here for the sake of clarity). The examination image used for this purpose is the examination image of the target object acquired in each individual case after time t3 and most recently prior to time t5. If no further examination image of the target object is acquired between times t4 and t5, the first examination image 7 may be used here to generate the auxiliary subtraction image 12.

Then, at time t5, the zoom level is changed. In this case, the zoom level is increased, so that a smaller image segment, e.g., a smaller sub-region of the target object is acquired or imaged. Immediately after the zoom level has been changed, a third mask image 13 is generated automatically at time t6. It is recognized here that the third mask image 13 represents a smaller sub-region of the target object than, for example, the auxiliary subtraction image 12 and the second subtraction image 8. In particular, the zoom level for the third mask image 13 is here selected depending on the first image content 9 or depending on the size thereof, so that the first image content 9 includes a large part of the third mask image 13. As a result, an improved depiction of detail of the first image content 9 and its immediate vicinity may be achieved in this changed zoom level. The third mask image 13 accordingly contains, in the image region acquired, the entire image content up to time t5 or t6, in particular, the first image content 9. Times t5 and t6 are so close together such that no additional or new further image content builds up between these times.

At time t7, a second examination image 14 of the target object is acquired. The third mask image 13 is subtracted from this second examination image 14 to generate the third subtraction image 15. The first image content 9 is no longer contained in the third subtraction image 15 and is therefore denoted by a dashed line here. If a second roadmap image 16 is now generated by applying the combination function 10 to the first subtraction image 5 and the third subtraction image 15, the image content built up until time t5 or t6, (in particular, the first image content 9), is therefore no longer visible therein.

At time t8, a third examination image 17 of the target object is acquired. A fourth subtraction image 18 is generated therefrom by subtraction of the third mask image 13. The first image content 9 is therefore not contained in the fourth subtraction image 18 either and is therefore also indicated here by a dashed line merely for better orientation. However, as some time has elapsed between points t6 and t8, further image content, namely a second image content 19, has built up since time t6, e.g., since the acquisition of the third mask image 13 up to time t8, which content is therefore contained in the third examination image 17, but not in the third mask image 13, and therefore remains visible in the fourth subtraction image 18. In this example, new radio- or X-ray-opaque glue has been introduced between times t7 and t8, which is now visible in the form of the second image content 19 in the fourth subtraction image 18.

A third roadmap image 20 may now be generated by applying the combination function 10 to the first subtraction image 5 and the fourth subtraction image 18. From an overall view of the roadmap images 11, 16, 20, a chronological development of the respective interventional procedure may therefore be reconstructed.

Figure 2:
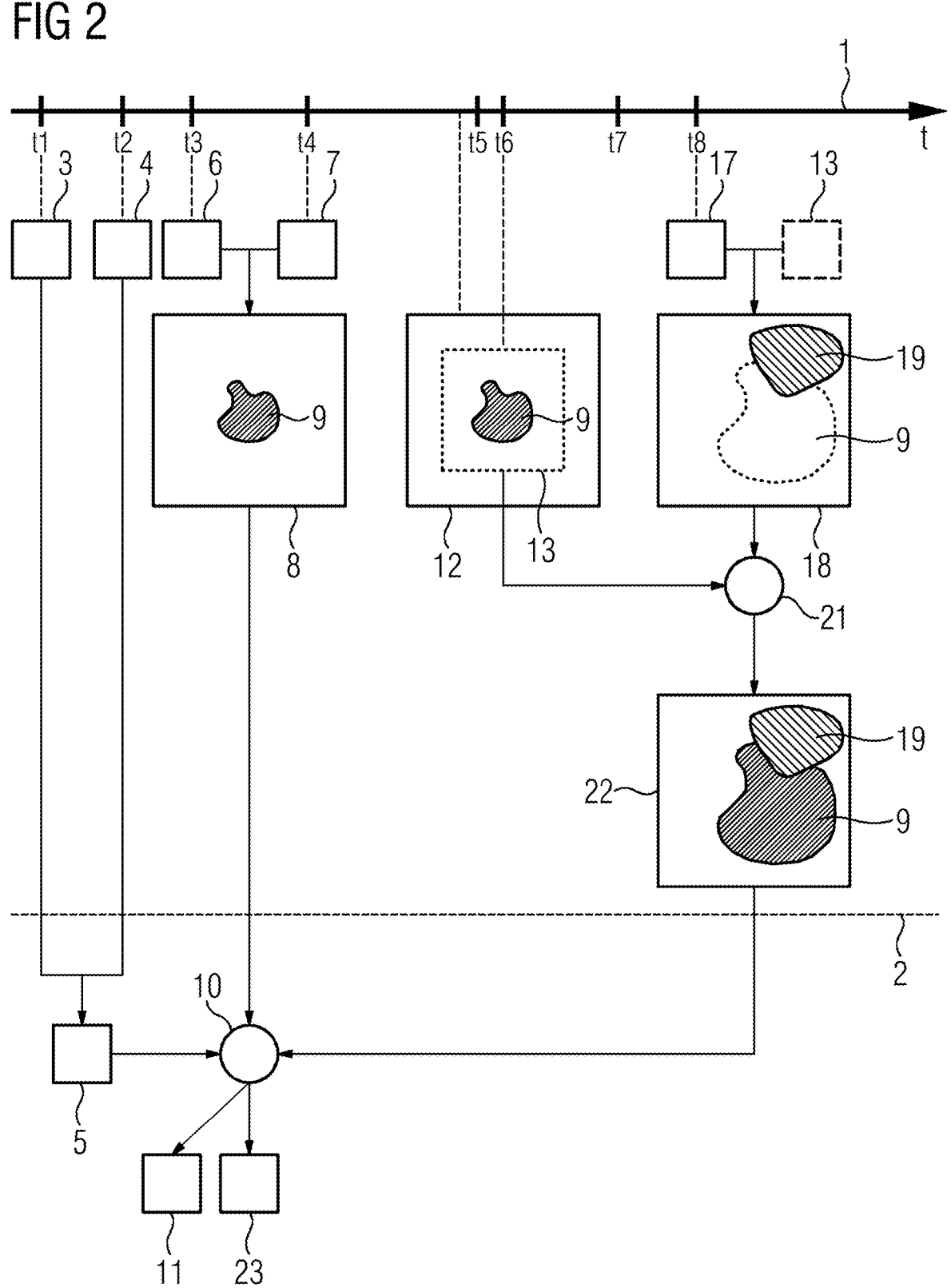
FIG. 2 depicts a schematic overview to illustrate a second variant of a method for generating an image of a target object.

FIG. 2 depicts a schematic overview illustrating a second variant of a method. The overview shown in FIG. 2 basically has the same structure as that shown in FIG. 1. Only the differences between the second variant of the method illustrated in FIG. 2 and the first variant of the method illustrated in FIG. 1 will therefore be explained.

In the second method variant shown in FIG. 2, the fourth subtraction image 18 and the auxiliary subtraction image 12 acquired or generated prior to the changing of the zoom level are combined with one another. For this purpose, a superimposition function 21 is applied to the auxiliary subtraction image 12 and the fourth subtraction image 18. Depending on requirements, the auxiliary subtraction image 12 and the fourth subtraction image 18 are added together, multiplied by one or more predefined or set factors, matched in color value and/or undergo thresholding for noise suppression at least in certain regions. As a result, the application of the superimposition function 21 produces a combined subtraction image 22. This combined subtraction image 22 therefore incorporates contributions from the second mask image 6, the examination image acquired most recently prior to time t5, the mask image 13 and the third examination image 17. Both the first image content 9 and the second image content 19 are therefore contained, (e.g., visible), in the combined subtraction image 22. The generation of the combined subtraction image 22 may therefore be expressed as:

$$DVK=F[DV(t5),DV(t8)],$$

where DVK(tx) denotes the combined subtraction image, F[ ] the superimposition function 21, DV(t5) the auxiliary subtraction image 12 and DV(t8) the fourth subtraction image 18.

The first subtraction image 5 and the combined subtraction image 22 are then combined with one another by applying the combination function 10, thereby producing a fourth roadmap image 23. The generation of the fourth roadmap image 23 may therefore be expressed according to the above notation as:

$$RDMP(t8)=K[VM,F[DV(t5),DV(t8)]].$$

The entire image content 9, 19 built up between time t3 and time t8 is now advantageously contained and visible in this fourth roadmap image 23. The development over time of the respective interventional procedure may therefore be traced, without image artifacts, across the changing of the zoom level at time t5 solely based on the fourth roadmap image 23.

Figure 3:
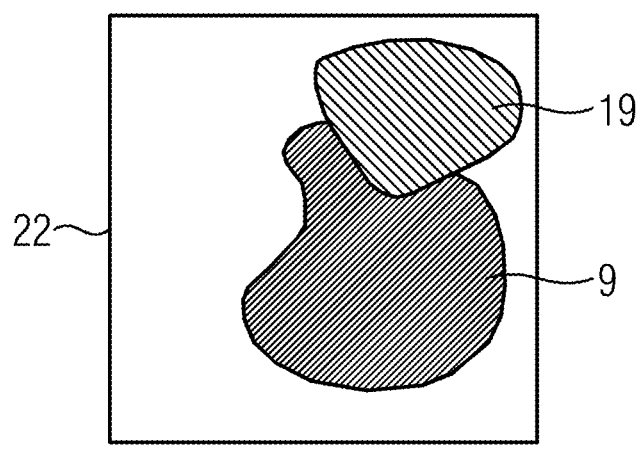
FIG. 3 schematically illustrates an example of a generated image of a target object.

FIG. 3 schematically illustrates the combined subtraction image 22 for the case that thresholding and/or color value matching for the first image content 9 and/or the second image content 19 or the corresponding image regions has been applied as part of the superimposition function 21. These actions provide a particularly simple method of visually differentiating between the first image content 9 and the second image content 19 in the combined subtraction image 22 and thus ultimately also in the fourth roadmap image 23. Therefore, not only may the entire image content 9, 19 built up between time t3 and time t8 may be read from the roadmap image 23 but also its development over time may be traced in a particularly simple manner based on the different representations.

In the figures, only the images 8, 12, 13, 15, 18, and 22 are shown with a corresponding image content 9, 19 by way of example, whereas the other images 3, 4, 5, 6, 7, 11, 14, 16, 17, 20, and 23 are merely indicated schematically. However, these schematically indicated images may self-evidently have the same size as the images 8, 12, 13, 18, and 22 shown with the corresponding image content 9, 19 by way of example and represent or map the target object in a corresponding manner. The individual elements shown in the figures therefore give no direct indication of the size of corresponding actual counterparts for a concrete implementation or realization of the method described.

The method described advantageously enables the zoom function or other imaging device function or functionality affecting the image acquisition conditions to be applied or used in the roadmap method. The use of the zoom function may advantageously provide improved recognizability of the image contents 9, 19. In existing digital systems, (e.g., imaging devices), widely used nowadays, the pixel size used does not change irrespective of the zoom level set. For improved recognizability, when the zoom level is changed, the imaging device or an X-ray beam cone is collimated to a smaller image format or a smaller image segment, e.g., a smaller sub-region of the target object. The radiation dose may also be increased to provide better recognizability. However, the total or skin dose exposure of the target object, (or more specifically the patient), is not increased by the smaller image format. However, the collimation causes scattered radiation conditions to change, for example. This is considered in the present method in that, to generate the subtraction images 15, 18 from the examination images 14, 17 acquired after time t6, the third mask image 13 likewise acquired after time t5 is used. This advantageously prevents the subtraction images 15, 18 generated from the examination images 14, 17 from becoming virtually unusable due to image artifacts resulting from the changing of the zoom level at time t5. If instead of the third mask image 13, for example, the second mask image 6 were to continue to be used even after time t5, it would be effectively impractical to use the zoom function in order to achieve an information gain in the region of the image contents 9, 19. The automated acquisition and the use of the third mask images 13 therefore makes it possible to respond during the method in a physically optimum manner to the new acquisition conditions then arising.

Although the disclosure has been illustrated and described in detail by the exemplary embodiments, the disclosure is not restricted by the disclosed examples and the person skilled in the art may derive other variations from this without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for generating at least one new roadmap image of a target object visualized by an imaging device, the method comprising:

generating a first subtraction image from a first mask image of the target object and a contrast agent image of the target object, wherein the first mask image has been acquired by the imaging device prior to introduction of a contrast agent, and wherein the contrast agent image has been acquired by the imaging device after introduction of the contrast agent;

generating a second subtraction image from a second mask image of the target object and a first examination image of the target object, wherein the second mask image and the first examination image have been acquired using a same parameter value of a physical parameter of the imaging device as the first mask image and the contrast agent image;

generating a first roadmap image by superimposition of the first subtraction image and the second subtraction image;

subsequently changing the parameter value of the physical parameter of the imaging device which affects an acquisition of images of the target object by the imaging device;

automatically acquiring a third mask image of the target object, immediately after the changing of the parameter value, by the imaging device using the changed parameter value;

subsequently acquiring at least one second examination image of the target object using the changed parameter value;

generating at least one third subtraction image of the target object from the at least one second examination image of the target object and the third mask image; and generating the at least one new roadmap image by superimposition of the first subtraction image generated prior to the changing of the parameter value of the physical parameter and the at least one third subtraction image generated after the changing of the parameter value of the physical parameter.

2. The method of claim 1, further comprising:

automatically generating an auxiliary subtraction image by subtracting the second mask image or the first mask image from an examination image of the target object acquired prior to the changing of the parameter value;

automatically generating a combined subtraction image by combining the auxiliary subtraction image with the third subtraction image; and generating the at least one new roadmap image using the combined subtraction image together with the first subtraction image.

3. The method of claim 2, further comprising, in response to receiving a control command to change the parameter value and prior to execution thereof:

automatically acquiring an auxiliary examination image of the target object by the imaging device; and using the auxiliary examination image as the examination image of the target object acquired prior to the changing of the parameter value for generating the auxiliary subtraction image.

4. The method of claim 3, wherein the auxiliary subtraction image and the combined subtraction image are generated as zero-mean images, so that a respective average of pixel values thereof is zero.

5. The method of claim 4, wherein the third subtraction image is added to the auxiliary subtraction image to generate the combined subtraction image.

6. The method of claim 4, wherein, to generate the combined subtraction image, pixel values of the auxiliary subtraction image are automatically multiplied by a factor other than 1 prior to the combining of the auxiliary subtraction image with the third subtraction image.

7. The method of claim 4, wherein, to generate the combined subtraction image, a color value of the auxiliary subtraction image, the third subtraction image, or both the auxiliary subtraction image and the third subtraction image is/are automatically changed so that a portion of the combined subtraction image originating from the auxiliary subtraction image has a display color different from that of the portion of the combined subtraction image originating from the third subtraction image.

8. The method of claim 4, wherein, to generate the combined subtraction image, prior to the combining of the auxiliary subtraction image with the third subtraction image:

an image region is automatically determined by comparison of the auxiliary subtraction image with the third subtraction image, wherein the third subtraction image has an image content not present in the auxiliary subtraction image, and a predefined threshold value filter is automatically applied to a sub-region of the auxiliary subtraction image corresponding to the image region for noise suppression.

9. The method of claim 2, wherein, to generate the auxiliary subtraction image:

a plurality of auxiliary examination images of the target object is acquired automatically by the imaging device after receiving a control command to change the parameter value and prior to execution thereof, and the plurality of auxiliary examination images is averaged in order to reduce noise in the auxiliary subtraction image.

10. The method of claim 9, wherein, to acquire the plurality of auxiliary examination images, an image acquisition frequency of the imaging device is automatically increased compared to a value used hitherto.

11. The method of claim 2, wherein the auxiliary subtraction image and the combined subtraction image are generated as zero-mean images, so that a respective average of pixel values thereof is zero.

12. The method of claim 2, wherein the third subtraction image is added to the auxiliary subtraction image to generate the combined subtraction image.

13. The method of claim 2, wherein, to generate the combined subtraction image, pixel values of the auxiliary subtraction image are automatically multiplied by a factor other than 1 prior to the combining of the auxiliary subtraction image with the third subtraction image.

14. The method of claim 2, wherein, to generate the combined subtraction image, a color value of the auxiliary subtraction image, the third subtraction image, or both the auxiliary subtraction image and the third subtraction image is/are automatically changed so that a portion of the combined subtraction image originating from the auxiliary subtraction image has a display color different from that of the portion of the combined subtraction image originating from the third subtraction image.

15. The method of claim 2, wherein, to generate the combined subtraction image, prior to the combining of the auxiliary subtraction image with the third subtraction image:

an image region is automatically determined by comparison of the auxiliary subtraction image with the third subtraction image, wherein the third subtraction image has an image content not present in the auxiliary subtraction image, and a predefined threshold value filter is automatically applied to a sub-region of the auxiliary subtraction image corresponding to the image region for noise suppression.

16. A data storage device having stored program code therein, wherein the program code, when executed by a processor device, is configured to cause the data storage device to:

generate a first subtraction image from a first mask image of a target object and a contrast agent image of the target object, wherein the first mask image has been acquired by an imaging device prior to introduction of a contrast agent, and wherein the contrast agent image has been acquired by the imaging device after introduction of the contrast agent;

generate a second subtraction image from a second mask image of the target object and a first examination image of the target object, wherein the second mask image and the first examination image have been acquired using a same parameter value of a physical parameter of the imaging device as the first mask image and the contrast agent image;

generate a first roadmap image by superimposition of the first subtraction image and the second subtraction image;

subsequently change the parameter value of the physical parameter of the imaging device which affects an acquisition of images of the target object by the imaging device;

acquire a third mask image of the target object, immediately after the changing of the parameter value, by the imaging device using the changed parameter value;

acquire at least one second examination image of the target object using the changed parameter value;

generate at least one third subtraction image of the target object from the at least one second examination image of the target object and the third mask image; and generate at least one new roadmap image by superimposition of the first subtraction image generated prior to the changing of the parameter value of the physical parameter and the at least one third subtraction image generated after the changing of the parameter value of the physical parameter.

17. An imaging device comprising:

a data processing device configured to automatically process target object images acquired by the imaging device, wherein the data processing device comprises a data storage device and a processor device connected thereto for executing program code stored in the data storage device, wherein the processor device is configured to:

generate a first subtraction image from a first mask image of a target object and a contrast agent image of the target object, wherein the first mask image has been acquired by the imaging device prior to introduction of a contrast agent, and wherein the contrast agent image has been acquired by the imaging device after introduction of the contrast agent;

generate a second subtraction image from a second mask image of the target object and a first examination image of the target object, wherein the second mask image and the first examination image have been acquired using a same parameter value of a physical parameter of the imaging device as the first mask image and the contrast agent image;

generate a first roadmap image by superimposition of the first subtraction image and the second subtraction image;

subsequently change the parameter value of the physical parameter of the imaging device which affects an acquisition of images of the target object by the imaging device;

acquire a third mask image of the target object, immediately after the changing of the parameter value, by the imaging device using the changed parameter value;

acquire at least one second examination image of the target object using the changed parameter value;

generate at least one third subtraction image of the target object from the at least one second examination image of the target object and the third mask image; and generate at least one new roadmap image by superimposition of the first subtraction image generated prior to the changing of the parameter value of the physical parameter and the at least one third subtraction image generated after the changing of the parameter value of the physical parameter.

18. The method of claim 1, wherein the physical parameter is a zoom level used for image acquisition, an aperture size, an aperature shape, a collimator setting, a voltage of an X-ray tube of the imaging device, a radiation output, or a radiation dose per image.

19. The method of claim 1, wherein the first roadmap image and the at least one new roadmap image provide a chronological development of an interventional procedure.

* * * * *